United States Patent [19]

Pitt et al.

[11] Patent Number: 5,270,161
[45] Date of Patent: Dec. 14, 1993

[54] NON-IONIC SURFACE ACTIVE COMPOUNDS

[75] Inventors: Alan R. Pitt, St. Albans; Ian M. Newington, High Wycombe, both of England

[73] Assignee: Eastman Kodak Company, Rochester, N.Y.

[21] Appl. No.: 730,965

[22] PCT Filed: Apr. 13, 1990

[86] PCT No.: PCT/EP90/00606
§ 371 Date: Jul. 29, 1991
§ 102(e) Date: Jul. 29, 1991

[87] PCT Pub. No.: WO90/12782
PCT Pub. Date: Nov. 1, 1990

[30] Foreign Application Priority Data
Apr. 26, 1989 [GB] United Kingdom ............... 8909576

[51] Int. Cl.⁵ .................... G03C 1/005; C07C 215/10
[52] U.S. Cl. ............................ 430/637; 106/287.26; 564/157; 564/158; 564/347; 564/348; 564/349; 564/504
[58] Field of Search ............. 564/349, 348, 347, 504; 252/308; 430/502, 637; 106/287.26

[56] References Cited

U.S. PATENT DOCUMENTS

| | | | |
|---|---|---|---|
| 2,761,791 | 9/1956 | Russel | 430/502 |
| 3,508,947 | 4/1970 | Hughes | 117/34 |
| 4,430,250 | 2/1984 | Sebag et al. | 252/351 |
| 4,599,090 | 7/1986 | Steckel | 44/63 |
| 4,808,755 | 2/1989 | Wirth et al. | 564/501 |

FOREIGN PATENT DOCUMENTS

| | | |
|---|---|---|
| 44025 | 7/1980 | European Pat. Off. |
| 46947 | 8/1980 | European Pat. Off. |
| 206998 | 12/1986 | European Pat. Off. |
| 53-127426 | 11/1978 | Japan |
| 54-163829 | 12/1979 | Japan |
| 54163829 | 12/1990 | Japan |
| 2153373 | 8/1985 | United Kingdom |

OTHER PUBLICATIONS

Chemical Abstract 167883 (DD 247,014), 1988.
Chemical Abstract 223509 Tenside Surfactants, 1988, 25(1), pp. 8-13.
Chemical Abstract 110888-45-4, 1987.
Chemical Abstract 110888-47-6, 1988.
Chemical Abstract 110888-49-8, 1988.
Chemical Abstract 116250-55-6, 1988.

*Primary Examiner*—Glennon H. Hollrah
*Assistant Examiner*—Shailendra Kumar
*Attorney, Agent, or Firm*—Paul A. Leipold

[57] ABSTRACT

Water-soluble, non-ionic surface active compounds are provided having the formula

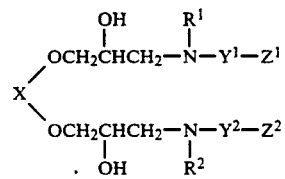

wherein
$R^1$ and $R^2$ are each independently hydrogen or an alkyl group having from 1 to 4 carbon atoms;
X is a hydrophobic substituted or unsubstituted arylene group or a hydrophobic substituted or unsubstituted alkylene group;
$Y^1$ and $Y^2$ are each independently a chemical bond, —CO— or —$(CH_2)_m NR^3 CO$—;
m is an integer from 1 to 6;
$R^3$ is as defined for $R^1$ and $R^2$; and,
$Z^1$ and $Z^2$ are each independently a hydrophilic polyhydroxyalkyl group. The compounds are particularly useful as coating aids for the coating of hydrophilic colloid layers in the preparation of photographic materials.

9 Claims, No Drawings

NON-IONIC SURFACE ACTIVE COMPOUNDS

The invention relates to non-ionic surface active compounds.

Japanese Patent Application No. 54/163829 describes low toxicity cosmetic compositions which contain a compound having the formula

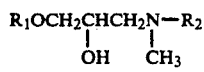

wherein $R_1$ is an alkyl or alkenyl group having from 10 to 22 carbon atoms and $R_2$ is a polyhydroxyalkyl group. The compounds can be dissolved or dispersed in water and oily cosmetic bases for the preparation of products such as milky lotions, face lotions, hair conditioners, shampoos and rinses.

It is desirable for a number of applications to use non-ionic surface active compounds which are more water-soluble than the compounds described above. Solubility affects the appearance of the surfactant solution e.g. a surfactant which is dispersible rather than soluble will result in a cloudy rather than a clear solution. Also, the solubility of the surfactant can affect its use e.g. for use as an effective coating aid in a hydrophilic colloid solution the surfactant must be soluble. The invention provides such surface active compounds.

The surface active compounds of the invention may be used as dispersants, emulsifiers, wetting agents and coating aids. In particular, the compounds may be used in the manufacture of photographic materials.

The invention provides a water-soluble, non-ionic surface active compound having the formula

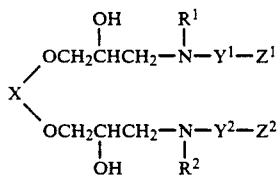

wherein
- $R^1$ and $R^2$ are each independently hydrogen or an alkyl group having from 1 to 4 carbon atoms;
- X is a hydrophobic substituted or unsubstituted arylene group or a hydrophobic substituted or unsubstituted alkylene group;
- $Y^1$ and $Y^2$ are each independently a chemical bond, —CO— or —$(CH_2)_m NR^3 CO$—;
- m is an integer from 1 to 6;
- $R^3$ is as defined for $R^1$ and $R^2$; and,
- $Z^1$ and $Z^2$ are each independently a hydrophilic polyhydroxyalkyl group.

When X is an arylene group it is preferably an alkyl substituted phenylene group. The alkyl substituent or substituents preferably have a total of from 6 to 18 carbon atoms. A particularly preferred substituted arylene group is represented by the formula

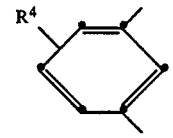

wherein $R^4$ is an alkyl group having from 6 to 18 carbon atoms. Specific examples of suitable alkyl substituents include 4—$C_6H_{13}$, 4—$C_{12}H_{25}$ and 5—$C_{15}H_{31}$.

When X is an alkylene group it preferably contains a total of from 6 to 23 carbon atoms. A particularly preferred alkylene group is represented by the formula

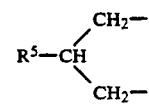

wherein $R^5$ is an alkyl group having from 3 to 20 carbon atoms. Specific examples of suitable alkyl substituents include —$C_6H_{13}$, —$C_{10}H_{21}$, —$C_{12}H_{25}$ and —$C_{15}H_{31}$.

Preferred polyhydroxyalkyl groups from which $Z^1$ and $Z^2$ may be selected include groups derived from sugars. For example, the polyhydroxyalkyl group may have the formula —$(CH_2)_n(CHOH)_p CH_2 OH$ wherein n is 0 or 1 and p is an integer from 3 to 6. Another example of a preferred polyhydroxyalkyl group is represented by the formula —$C(CH_2OH)_3$.

Preferably, the compounds do not contain polyether linkages.

Specific examples of compounds of the invention are as follows

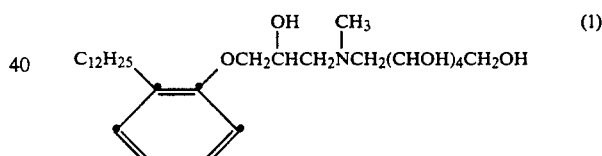

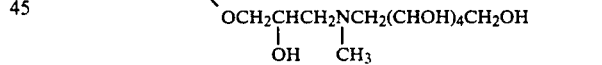

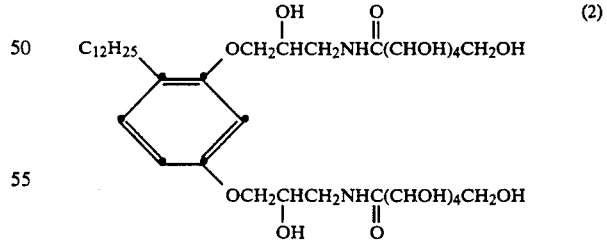

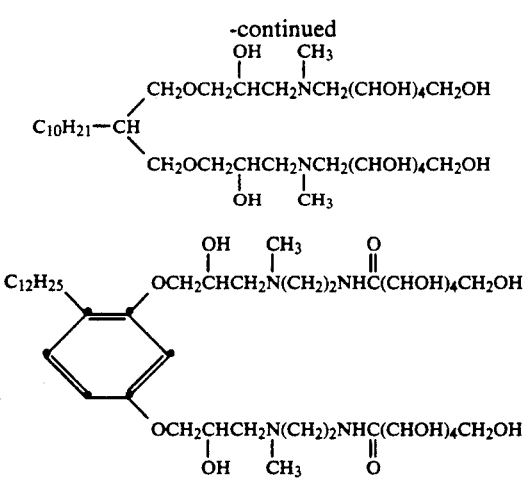

(4)

(5)

The compounds of the invention may be prepared from known dihydroxy compounds having the formula HO—X—OH wherein X is as defined above. Reaction of the dihydroxy compound with epibromohydrin provides a bisepoxide intermediate compound as follows:

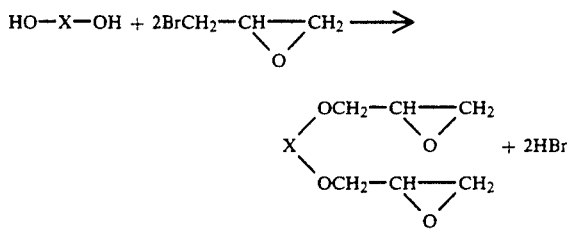

From the bisepoxide intermediate compound, various routes may be taken to produce the compounds of the invention. For example, the bisepoxide may be reacted with an amine having the formula $Z^1$—$NR^1H$ or $Z^1$—$CONH(CH_2)_mNR^1H$ wherein $Z^1$, $R^1$ and m are as defined above. Alternatively, the bisepoxide may be converted to the corresponding bisamine either by reaction with ammonia or by reaction with sodium azide with subsequent reduction. The resulting bisamine can be reacted with a polyhydroxyalkyl ester e.g. a sugar lactone, to provide a compound of the invention having amide links between the polyhydroxyalkyl groups and the bisamine residue.

Details of the reaction conditions used for making the compounds of the invention are to be found in the specific examples given later in the specification.

The compounds of the invention may be used as emulsifying agents. For example, stable oil-in-water emulsions can be prepared by mixing the oil and water together in the presence of a compound of the invention. Examples of oils which can be emulsified in this way include hydrocarbons such as dodecane and pentadecane.

The compounds of the invention may be used as coating aids in aqueous hydrophilic colloid compositions e.g. a gelatin solution. In a particular application, the compounds may be used in the preparation of light sensitive photographic materials. Such a material comprises a support having thereon at least one layer comprising a hydrophilic colloid and a compound of the invention.

In the preparation of a photographic material, it is usual to coat a support with one or more layers comprising an aqueous solution of a hydrophilic colloid binder e.g. gelatin. Such layers include, for example, silver halide emulsion layers, intermediate layers, antihalation layers, filter layers, antistatic layers and protective layers. For multilayer materials, the layers may be coated simultaneously on conventional photographic supports as described in U.S. Pat. Nos. 2,761,791 and 3,508,947.

In producing the thin hydrophilic colloid layers of such photographic materials, it is required that coating solutions are coated uniformly without the formation of repellency spots or craters, hereinafter referred to as repellencies. A repellency is a round, oval-shaped or comet-shaped indentation or crater in the layer or one or more of the layers coated and is usually produced by the presence of small particles or droplets of insoluble materials in the form of addenda, impurities or contaminants which are in contact with the uppermost liquid-air interface of the coated layer(s) and have surface activity (i.e. are capable of reducing the surface tension of the liquid-air interface during the coating process).

Solutions coated in the preparation of photographic materials often contain dispersed, insoluble photographic addenda, which might include organic solvents, or addenda to alter certain physical properties, which might include lubricants, each of which may be capable of imparting repellencies to the coated layer(s). Even photographic gelatin may contain insoluble residues of naturally-occuring animal fats and fatty acids which are capable of imparting repellencies to the coated layer(s). Also, surface active contaminants may originate from external sources during the preparation of the coating composition or during coating. For example, the layer(s) being coated, or immediately after coating, may be unintentionally showered by droplets of lubricating oils used in the apparatus.

In one aspect of the invention, a surface active compound of the invention is used as a coating aid in the formation of a hydrophilic colloid layer. Preferably, the coating aid is used in an amount from 0.01 to 0.30, more preferably from 0.05 to 0.20, weight % based on the weight of the hydrophilic colloid coating composition. The range of concentration within which the coating aid is used depends on the source of repellency. It also depends on whether other surface active agents are present.

The preferred hydrophilic colloid is gelatin e.g. alkali-treated gelatin (cattle bone or hide gelatin) and acid-treated gelatin (pigskin gelatin) or a gelatin derivative e.g. acetylated gelatin and phthalated gelatin. Other suitable hydrophilic colloids include naturally occurring substances such as proteins, protein derivatives, cellulose derivatives e.g. cellulose esters, polysaccharides e.g. dextran, gum arabic, zein, casein and pectin, collagen derivatives, agar-agar, arrowroot and albumin. Examples of suitable synthetic hydrophilic colloids include polyvinyl alcohol, acrylamide polymers, maleic acid copolymers, acrylic acid copolymers, methacrylic acid copolymers and polyalkylene oxides.

In the following discussion concerning the nature of photographic materials, reference will be made to Research Disclosure, December 1978, Item 17643, published by Industrial Opportunities Ltd., The Old Harbourmaster's, 8 North Street, Emsworth, Hants P010 7DD, U.K. This publication will be identified hereafter as "Research Disclosure".

The photographic material may comprise a negative-working or positive-working silver halide emulsion layer. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

For colour photographic materials, references giving information on couplers and on methods for their dispersions are given in Sections VII and XIV, respectively, of Research Disclosure. An account of dye-forming development is given in 'Modern Photographic Processing', Vol. 2, Grant Haist, Wiley, New York, 1978, Chapter 9.

The photographic materials or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic materials can be coated on a variety of supports as described in Research Disclosure Section XVII and the references described therein.

The photographic materials can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a colour developing agent to reduce developable silver halide and oxidize the colour developing agent. Oxidized colour developing agent in turn reacts with the coupler to yield a dye.

With negative working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Specific examples of the preparation of compounds of the invention are as follows.

PREPARATION OF COMPOUND (1)

4-Dodecylresorcinol (36.0mmol) was added to a suspension of sodium hydride (79.0mmol) in dry dimethylformamide (250 ml). After stirring at 20° C. for 45 minutes, epibromohydrin (79.0mmol) was added and the mixture stirred for a further 18 hours. Water (700 ml) was added and the product extracted into ethyl acetate. The solution was washed with water, dried over magnesium sulphate, filtered and concentrated at reduced pressure. The bisepoxide was isolated after purification by chromatography on silica gel (diethyl ether-petrol gradient) as a white solid (86% yield).

Found: C, 73.89; H, 10.03.
$C_{24}H_{38}O_4$ requires: C, 73.81; H, 9.81.

The bisepoxide (5.0mmol) was dissolved in t-butanol (75 ml) with N-methyl-D-glucamine (10.0mmol). The solution was heated under reflux for 24 hours, cooled and the solvent removed under reduced pressure to give Compound (1) as a hygroscopic white solid foam.

Found: C, 57.74; H, 9.23; N, 3.57.
$C_{38}H_{72}N_2O_{14}.\frac{1}{2}H_2O$ requires: C, 57.77; H, 9.31; N, 3.55.

PREPARATION OF COMPOUND (3)

The same bisepoxide (5.0mmol) used in the preparation of Compound (1) was dissolved in t-butanol (75 ml) with tris(hydroxymethyl)aminomethane (10.0mmol). The solution was heated under reflux for 24 hours, cooled and the solvent removed under reduced pressure to give the product surfactant as a hygroscopic solid foam.

Found: C, 59.89; H, 9.57; N, 4.32.
$C_{32}H_{60}N_2O_{10}.\frac{1}{2}H_2O$ requires: C, 59.88; H, 9.58; N, 4.36.

PREPARATION OF COMPOUND (4)

A solution of diethyl malonate (28 ml, 186mmol) in ethanol (20 ml) was added slowly to a solution of sodium (4.2g. 180mmol) in ethanol (175 ml) under reflux. This was followed by addition of 1-bromodecane (38.0g, 155mmol) after which reflux was continued for a further 3 hours before cooling. The suspension was filtered and the filtrate evaporated under reduced pressure. The crude product was partitioned between ethyl acetate (300 ml) and water (200 ml) and the organic layer dried over magnesium sulphate and evaporated. The product was purified by vacuum distillation to give 2-decyldiethylmalonate as a colourless liquid (37.5g, 67%) b.p. 127°–130° C. at 0.05mbar.

2-Decyldiethylmalonate (20.0g, 67mmol) in diethyl ether (30 ml) was added dropwise to a suspension of lithium aluminium hydride (10.1g, 268mmol) in diethyl ether (800 ml) and the mixture stirred for 24 hours at 20° C. The reaction was quenched with 2N hydrochloric acid and the organic layer separated, dried over magnesium sulphate and evaporated to give 2-decyl-1,3-propanediol as a white solid (14.1g, 98%).

2-Decyl-1,3-propanediol (14.0g, 65mmol) was dissolved in diethyl ether-hexane (200ml:600ml) and treated with epibromohydrin (12.3 ml, 144 mmol), tetrabutylammonium hydrogen sulphate (2.0g) and a solution of sodium hydroxide (140 g) in water (150 ml). The mixture was stirred vigorously for 72 hours, the organic layer separated, dried over magnesium sulphate and evaporated. The product was purified by chromatography on silica gel (63–200μm grade) in a diethyl ether petrol gradient to give the bisepoxide as a colourless oil (5.4g, 26%).

Found: C, 69.39; H, 11.01.
$C_{19}H_{36}O_4$ requires: C, 69.47; H, 11.05.

The bisepoxide (1.0 g 3.0mmol) was dissolved in t-butanol (30 ml) with N-methyl-D-glucamine (1.2g, 6.0mmol) and heated under reflux for 24 hours, cooled, and the solvent evaporated under reduced pressure to give the product surfactant as a viscous gum.

Found: C, 54.29; H, 9.68; N, 3.71.
$C_{33}H_{70}N_2O_{14}.\frac{1}{2}H_2O$ requires: C, 54.45; H, 9.83; N, 3.85.

PREPARATION OF COMPOUND (5)

N-Methylethylenediamine (5.0g, 68mmol) with D-gluconolactone (12.0 g, 68 mmol) were dissolved in methanol (200 ml) and heated under reflux for 20 hours. The solvent was reduced to half volume and the solution stored at 4° C. for 48 hours. The solid product was filtered off, washed with a little methanol, and dried at 45° C. under vacuum to give a white solid (10.35 g, 61%) m.p. 116°-120° C.

This material (1.3 g, 5.2 mmol) was added to a solution of the same bisepoxide used in the preparation of Compound (1) (1.0 g. 2.6 mmol) in t-butanol (30 ml) and the solution heated under reflux for 18 hours. The solvent was evaporated to give a white solid foam.

Found: C, 55.45; H, 8.63; N, 6.01.
$C_{44}H_{78}N_4O_{16}.\frac{1}{2}H_2O$ requires: C, 55.80;
H, 8.81; N, 6.20.

The invention is further illustrated having regard to the following examples.

EXAMPLE 1

The solubility of the compounds of the invention was demonstrated by preparing 1% by weight solutions of the following compounds:

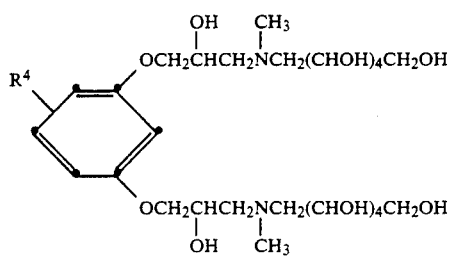

wherein $R^4=4-C_6H_{13}$, $4-C_{12}H_{25}$ and $5-C_{15}H_{31}$;

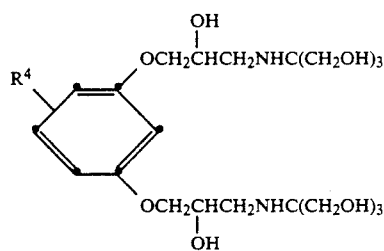

wherein $R^4=4-C_6H_{13}$, $4-C_{12}H_{25}$ and $5-C_{15}H_{31}$; Compound (2), Compound (4) and Compound (5).

All the compounds listed above dissolved in water to give clear solutions.

By way of comparison, the solubility of prior art compounds was demonstrated by attempting to dissolve 1% by weight of the following compounds in water:

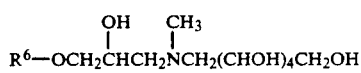

wherein $R^6=C_{12}H_{25}$, $C_{16}H_{33}$ and $C_{18}H_{37}$; and

The prior art compounds were either dispersible in water and formed cloudy dispersions, or formed crystals.

EXAMPLE 2

The ability of a compound of the invention to control repellencies caused by an impurity often found in hydrophilic colloid coating compositions was tested as follows.

Two gelatin layers, the uppermost of which contained one of the surfactants listed below in Table 1 as a coating aid, were coated onto a polyethylene terephthalate film base subbed to give good adhesion to gelatin. The bottom layer consisted of a 4% by weight solution of lime-processed bone gelatin in water coated at 85.4 ml/m². The top layer consisted of a 7% by weight solution of lime-processed bone gelatin in water containing a coloured dye marker, 1ppm oleic acid emulsified in small droplet form to induce repellency, and surfactant at one of the concentrations indicated in Table 1. The top layer was applied at a coverage of 14.2 ml/m². Both layers were applied simultaneously at a temperature of 40° C. using a conventional double slide hopper with applied suction and a linear coating speed of 15.25 m/min.

TABLE 1

| Surfactant | Concentration (% by weight) |
| --- | --- |
| Compound (1) | 0.03 |
|  | 0.10 |
|  | 0.30 |
| Compound (3) | 0.03 |
|  | 0.10 |
|  | 0.30 |

Each coating was free from repellencies in the tests whereas in the absence of surfactant the coating contained many repellencies.

EXAMPLE 3

The suitability of compounds of the invention as emulsifying agents was demonstrated by the preparation of oil-in-water emulsions.

Compound (1) was made into a 1% by weight aqueous solution and the solution was mixed with various amounts of dodecane and, independently, pentadecane. The surfactant was used in amounts to provide oil:surfactant ratios (by weight) of 1:2, 1:1 and 5:1. Emulsions were prepared by thorough mixing with an ultrasonic mixer for 5 minutes.

In each instance, emulsions were formed which were stable without creaming over a period of hours.

We claim:

1. A water-soluble, non-ionic surface active compound having the formula

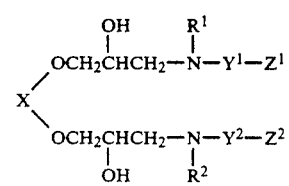

wherein
$R^1$ and $R^2$ are each independently hydrogen or an alkyl group having from 1 to 4 carbon atoms;

X is, a hydrophobic alkyl or alkyl substituted or unsubstituted arylene group $Y^1$ and $Y^2$ are each independently a chemical bond, $Z^1$ and $Z^2$ are each independently a hydrophilic polyhydroxyalkyl group.

2. A compound according to claim 1 wherein X is an alkyl substituted phenylene group.

3. A compound according to claim 2 wherein X is represented by the formula

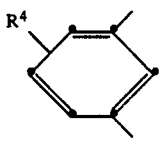

wherein $R^4$ is an alkyl group having from 6 to 18 carbon atoms.

4. A compound according to claim 1 wherein each of $Z^1$ and $Z^2$, independently, is represented by the formula $-(CH_2)_n(CHOH)_pCH_2OH$ wherein n is 0 or 1 and p is an integer from 3 to 6, or is represented by the formula $-C(CH_2OH)_3$.

5. A coating composition comprising a hydrophilic colloid and a surface active compound characterized in that the surface active compound is a compound according to claim 4.

6. A composition according to claim 5 wherein the hydrophilic colloid is gelatin.

7. A photographic material comprising a support having thereon at least one layer comprising a hydrophilic colloid and a surface active compound characterized in that the surface active compound is a compound according to claim 4.

8. A photographic material according to claim 7 comprising at least one photosensitive silver halide emulsion layer.

9. The compound of claim 1 comprising

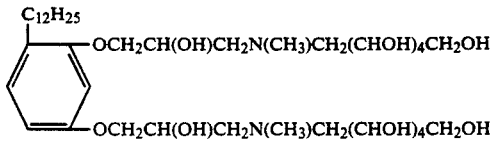

* * * * *